(12) United States Patent
Dhawan et al.

(10) Patent No.: US 8,580,910 B2
(45) Date of Patent: *Nov. 12, 2013

(54) 2,4,5-TRIAMINOPHENOLS AND RELATED COMPOUNDS

(75) Inventors: Rajiv Dhawan, Wilmington, DE (US); Annalisa Hargis, Wilmington, DE (US); Joachim C Ritter, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/517,261

(22) PCT Filed: Dec. 21, 2010

(86) PCT No.: PCT/US2010/061670
§ 371 (c)(1),
(2), (4) Date: Sep. 26, 2012

(87) PCT Pub. No.: WO2011/087809
PCT Pub. Date: Jul. 21, 2011

(65) Prior Publication Data
US 2013/0012741 A1    Jan. 10, 2013

Related U.S. Application Data

(60) Provisional application No. 61/288,469, filed on Dec. 21, 2009.

(51) Int. Cl.
*C08G 64/00* (2006.01)
*C08G 63/02* (2006.01)

(52) U.S. Cl.
USPC ............ 528/186; 528/210; 562/476; 564/418

(58) Field of Classification Search
USPC .................... 528/186, 210; 562/476; 564/418
See application file for complete search history.

(56) References Cited

U.S. PATENT DOCUMENTS

| | | | |
|---|---|---|---|
| 2013/0012679 A1* | 1/2013 | Dhawan et al. | ................ 528/186 |
| 2013/0046109 A1* | 2/2013 | Dhawan et al. | ................ 562/476 |

* cited by examiner

*Primary Examiner* — Terressa Boykin

(57) ABSTRACT

New triaminophenol compositions and related compounds are disclosed, as are processes for their preparation and for the preparation of novel salts and diacid complexes from such compounds. Polymers prepared from these compositions can be made into high strength fiber, film, and tape and are useful in applications such as protective apparel, aircraft, automotive components, personal electronics, and sports equipment.

10 Claims, No Drawings

2,4,5-TRIAMINOPHENOLS AND RELATED COMPOUNDS

This application claims priority under 35 U.S.C. §119(e) from, and claims the benefit of, U.S. Provisional Application No. 61/288,469, filed Dec. 21, 2009, which is by this reference incorporated in its entirety as a part hereof for all purposes.

FIELD OF DISCLOSURE

This disclosure relates to new compositions based on 2,4,5-triaminophenols, which can be used in the manufacture of high-performance polybenzimidazole polymers.

BACKGROUND

Aromatic amines and phenols are useful as monomers for high performance polymers such as aramid polymers and polybenzarenazoles. The structure of the specific monomer used greatly impacts polymer properties such as tenacity, solubility, and also the rheological behavior of the polymer during processing such as spinning. It is thought that replacing highly symmetric monomers that are currently used (e.g., 2,3,5,6-tetraminopyridine) with asymmetric monomers would increase the solubility of the corresponding polymers and the ease with which they are processed. However, such monomers are often difficult to synthesize or are unknown. These materials are unknown and have not been synthesized.

There is a need for asymmetric monomers that can be readily synthesized and used in the production of high performance polymers such as aramid polymers and polybenzarenazoles.

SUMMARY

In one embodiment, the inventions hereof provide a process comprising the steps (a1) monoaminating a composition described by Formula (X),

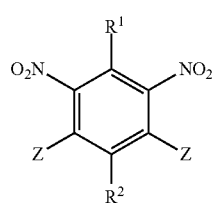

X wherein each Z is independently Cl or Br and $R^1$ and $R^2$ are each independently H, alkyl, or aryl; by heating a suspension of the composition of Formula (X) in solvent to a temperature in the range of about 60° C. to about 140° C. and contacting it with an aqueous solution of at least 2.0 equivalents $HNR^7R^8$ to produce a composition of Formula (XI), wherein $R^7$ and $R^8$ are each independently H, alkyl or aryl, or may be joined to form an aliphatic ring structure;

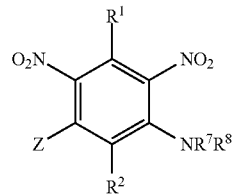

XI (b1) reacting the composition of Formula (XI) with benzyl alcohol and at least 1.0 equivalent of NaOH or of sodium henzyloxicle to produce a composition of Formula (XII);

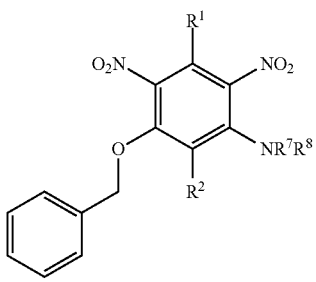

XII (c1) hydrogenating the composition of Formula (XII) by contacting the reaction mixture formed in step (b1) with hydrogen at a pressure in the range of about 0.31 to about 3.45 MPa and a temperature in the range of about 20° C. to about 100° C. for sufficient time to hydrogenate the composition of Formula (XII), thereby producing a reaction mixture comprising a composition of Formula (IX) and toluene

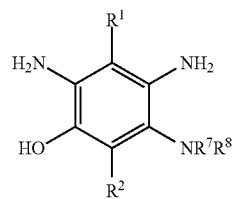

IX (d1) the reaction mixture formed in step (c1) with an aqueous solution comprising 1 to 2 equivalents of acid per mol of 2,4,5-triaminophenol and, optionally, heating the solution, thereby dissolving the 2,4,5-triaminophenol;

(e1) filtering the reaction mixture, thereby removing the spent hydrogenation catalyst;

(f1) extracting the toluene from the reaction mixture; and (g1) adjusting the pH of the extracted, filtered reaction mixture to a value between about 5 and about 7, by adding a base wherein said base does not increase the solubility of the Formula (IX) composition, thereby precipitating the composition of Formula (IX) from the reaction mixture.

DESCRIPTION

The following description is exemplary and explanatory only and is not restrictive of the invention, as defined in the appended claims.

The disclosures herein include new triaminophenols and related compounds, processes for the preparation of such triaminophenols and related compounds, processes for the preparation of products into which such triaminophenols and related compounds can be converted, and the products obtained and obtainable by such processes.

In the description of the subject matter of this application, the following definitional structure is provided, and, unless indicated to the contrary, is to be applied to the following terminology as employed herein:

As used herein, the term "free base," as applied to a triaminophenol, is used to denote a triaminophenol compound per se, for example, Formula (I)

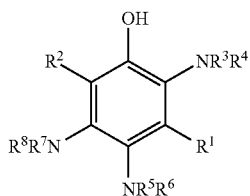

I to distinguish it from the acid salt of a triaminophenol or a complex of the triaminophenol with a diacid.

As used herein, the term "triaminophenol salt" or "[specific triaminophenol name or formula reference] salt," e.g., "Formula (IV) salt" or "TAPH salt" where TAPH means 2,4,5-triamino phenol, denotes a compound formed by reaction of a triaminophenol with "n" equivalents of an acid ("A") such as HCl, acetic acid, $H_2SO_4$, or $H_3PO_4$. One example of a triaminophenol salt is TAPH.2HCl (n=2, A=HCl). The salt may also be a hydrate; one such example is TAPH.3HCl).$xH_2O$.

As used herein, the term "triaminophenol complex" or "[specific triaminophenol name] [diacid source name] complex denotes a compound formed by reaction of a triaminophenol with a diacid source. Where the complex is to be used as a monomer in a polymerization, it can also be referred to as a "monomer complex." One example of a triaminophenol complex is TAPH.TA, wherein "TAPH" is 2,4,5-triaminophenol and "TA" is terephthalic acid. (n=2, A=HCl).

As used herein the term "diacid source" refers to the diacid HOOC-Q-COOH itself, disodium salt of HOOC-Q-COOH, a dipotassium salt of HOOC-Q-COOH, or mixtures thereof, wherein Q is a $C_6$ to $C_{20}$ substituted or unsubstituted monocyclic or polycyclic aromatic nucleus.

As used herein, the term "XYTA" denotes 2-X-5-Y-terephthalic acid, where X and Y each independently selected from the group consisting of H, OH, SH, $SO_3H$, methyl, ethyl, F, Cl, and Br. One example is 2,5-dihydroxyterephthalic acid ("DHTA"), in which X=Y=OH. The disodium dipotassium salt of the XYTA diacid can be represented by the term "$M_2XYTA$" where M is Na or K.

As used herein, the term "oleum" denotes fuming sulfuric acid, which is anhydrous and is formed by dissolving excess sulfur trioxide ($SO_3$) into sulfuric acid.

As used herein, the term "weak base" denotes a base whose pKa at 25° C. is between about 6 and about 11. Such a base has a pKa sufficient to react with the HCl, but not to deprotonate the phenolic proton.

As used herein, the term "net yield" of P denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

As used herein, the term "alkyl" denotes (a) a $C_1\sim C_{12}$, or $C_1\sim C_8$, $C_1\sim C_6$, or $C_1\sim C_4$, straight-chain or branched, saturated or unsaturated, substituted or unsubstituted, hydrocarbyl radical; or (b) a $C_3\sim C_{12}$, or $C_3\sim C_6$, cyclic aliphatic, saturated or unsaturated, substituted or unsubstituted, hydrocarbyl radical that is either bonded directly to the ring or to N or O, or is bonded to the ring or to N or O through a $C_1\sim C_6$ straight-chain or branched, saturated or unsaturated, substituted or unsubstituted, hydrocarbyl radical. A $C_4\sim C_{42}$ straight-chain or branched, saturated or unsaturated, substituted or unsubstituted, hydrocarbyl radical suitable for use herein may include, for example, a methyl, ethyl, n-propyl, i-propyl, n-butyl, sec-butyl, tort-butyl, n-pentyl, n-hexyl, n-octyl, trimethylpentyl, allyl and propargyl radical. An unsaturated aliphatic radical may include one or more double bonds, such as in a dienyl or terpenyl structure, or a triple bond such as in an acetylenyl structure. A $C_3\sim C_{12}$ cyclic aliphatic, saturated or unsaturated, substituted or unsubstituted, hydrocarbyl radical suitable for use herein may include, for example, an alicyclic functional group containing in its structure, as a skeleton, cyclohexane, cyclooctane, norbornane, norbornene, perhydro-anthracene, adamantane, or tricyclo-[$5.2.1.0^{2.6}$]-decane groups.

As used herein, the term "aryl" denotes a $C_6\sim C_{12}$, or $C_6\sim C_{10}$, aromatic substituted or unsubstituted hydrocarbyl radical that is either bonded directly to the ring or to N or O, or is bonded to the ring or to N or O through a $C_1\sim C_6$ straight-chain or branched, saturated or unsaturated, substituted or unsubstituted, hydrocarbyl radical. A $C_6\sim C_{12}$ aromatic substituted or unsubstituted hydrocarbyl radical suitable for use herein may include, for example, a radical derived from a benzyl, phenyl, biphenyl, naphthyl, anthracenyl, xylyl, toluoyl or cumenyl structure; including, for example, a phenyl, methylphenyl, ethylphenyl, n-propylphenyl, n-butylphenyl, t-butylphenyl, p-chlorophenyl, p-bromophenyl, naphthyl or ethyl naphthyl radical.

As used herein the term "unsubstituted hydrocarbyl radical" contains no atoms other than carbon and hydrogen.

As used herein, the term "substituted hydrocarbyl radical" is defined as a radical in which
- one or more heteroatoms selected from O, N, S and P may optionally be substituted for any one or more of the in-chain (i.e. non-terminal) or in-ring carbon atoms, provided that each heteroatom is separated from the next closest heteroatom by at least one and preferably two carbon atoms, and that no carbon atom is bonded to more than one heteroatom; and/or
- one or more halogen atoms may optionally be bonded to a terminal carbon atom.

In addition, however, a substituted $C_3\sim C_{12}$ cyclic aliphatic, saturated or unsaturated hydrocarbyl radical, or a substituted $C_6\sim C_{12}$ aromatic hydrocarbyl radical, may contain one or more $C_1\sim C_8$, or straight-chain or branched, saturated or unsaturated, hydrocarbyl radicals bonded to a carbon atom in the ring structure, such radical itself optionally being substituted with one or more heteroatoms selected from O, N, S and P, and/or containing one or more halogen atoms, subject to the conditions set forth above.

In various embodiments of this invention, new compounds or compositions represented by the structures of Formulas (I) through (V) below are provided.

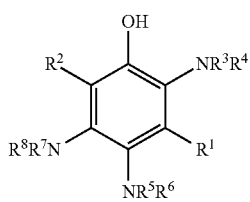

I

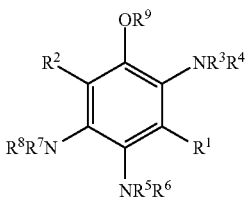

II

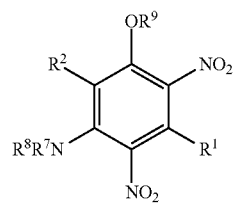

III

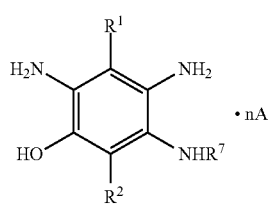

IV

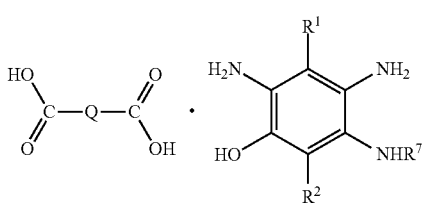

V

Also provided are novel polymers or polymer compositions comprising repeat units represented by Formula (VI).

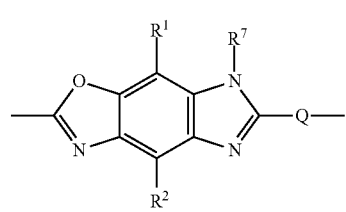

VI

In Formulas (I) through (VI), $R^1$ and $R^2$ are each independently H, alkyl, or aryl;

$R^3$ and $R^4$ are each independently H, alkyl or aryl or may be joined to form an aliphatic ring structure;

$R^5$ and $R^6$ are each independently H, alkyl or aryl or may be joined to form an aliphatic ring structure;

$R^7$ and $R^8$ are each independently H, alkyl or aryl or may be joined to form an aliphatic ring structure;

$R^9$ is n-propyl, isopropyl, a $C_4$ to $C_{18}$ tertiary alkyl, or a $C_7$ to $C_{18}$ substituted or unsubstituted benzyl;

n is 1 to 10;

A is an acid, e.g., HCl, acetic acid, $H_2SO_4$, or $H_3PO_4$; and

Q is a $C_6$ to $C_{20}$ substituted or unsubstituted monocyclic or polycyclic aromatic nucleus.

In one embodiment of the composition represented by Formula (I), $R^1$, $R^2$, $R^3$, $R^4$, $R^5$, $R^6$, $R^7$, and $R^8$ are each H. This compound (Formula (VII)) is 2,4,5-triaminophenol ("TAPH").

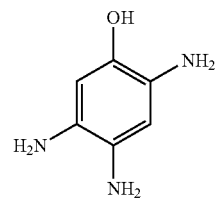

VII

In another embodiment of the composition represented by Formula (I), $R^4$ and $R^2$ are each independently H, alkyl, or aryl, $R^3$ is H, $R^4$ is alkyl or H, and, of the four groups $R^5$, $R^6$, $R^7$, and $R^8$, any three are H and the fourth is H, alkyl, or aryl. An example of this embodiment is shown below:

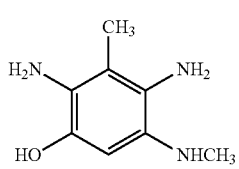

VIII

In another embodiment, a process is provided for preparing compositions of Formula (I) wherein each of $R^3$, $R^4$, $R^5$, and $R^6$ is H, represented by Formula (IX)

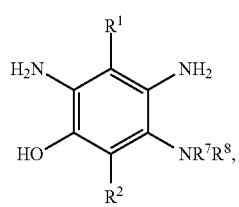

IX by
(a1) monoaminating a composition of Formula (X),

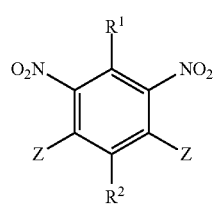

X wherein each Z is independently Cl or Br, by heating a suspension of the composition of Formula (X) in solvent to a temperature in the range of about 60° C. to about 140° C. and contacting it with an aqueous solution of at least 2.0 equivalents $HNR^7R^8$ to produce a composition of Formula (XI)

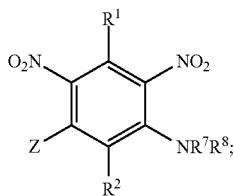

XI (b1) reacting the composition of Formula (XI) with benzyl alcohol and at least 1.0 equivalent of NaOH or of sodium benzyloxide to produce a composition of Formula (XII);

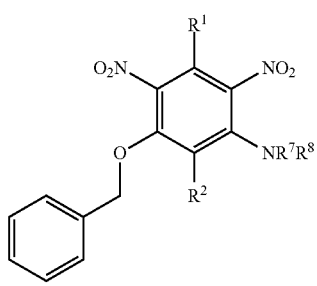

XII (c1) hydrogenating the composition of Formula (XII) by contacting the reaction mixture formed in step (b1) with hydrogen at a pressure in the range of about 0.31 to about 3.45 MPa and a temperature in the range of about 20° C. to about 100° C. for sufficient time to hydrogenate the composition of Formula (XII), thereby producing a reaction mixture comprising a composition of Formula (IX) and toluene;

(d1) contacting the reaction mixture formed in step (c1) with an aqueous solution comprising 1 to 2 equivalents of acid per mol of 2,4,5-triaminophenol and, optionally, heating the solution, thereby dissolving the 2,4,5-triaminophenol;

(e1) filtering the reaction mixture, thereby removing the spent hydrogenation catalyst;

(f1) extracting, the toluene from the reaction mixture; and (g1) adjusting the pH of the extracted, filtered reaction mixture to a value between about 5 and about 7, by adding a base wherein said base does not increase the solubility of the Formula (IX) composition, thereby precipitating the composition of Formula (IX) from the reaction mixture.

The composition represented by Formula (X) may be prepared by nitration of the corresponding dihalobenzene according to the method described in copending U.S. patent application Ser. No. 12/335,959, which is hereby incorporated by reference in its entirety for all purposes; by admixing a dihalobenzene represented by the structure of Formula (XIII)

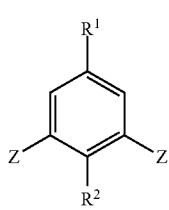

XIII wherein each Z is independently Cl or Br, with nitric acid, sulfuric acid, and oleum or $SO_3$, to form a reaction mixture that is characterized by (i) a concentration of nitric acid therein that is in the range of about 2.0 to about 2.3 moles per mole of dihalobenzene; (ii) a concentration of $SO_3$ therein that is in the range of about 1 to about 3 moles per mole of dihalobenzene; (iii) a concentration of dihalobenzene therein that is in the range of about 12 to about 24 weight percent; and (iv) a temperature of up to about 120° C.; and stirring the reaction mixture at a temperature in the range of about −10° C. to about 70° C. to form a dihalodinitrobenzene product represented by the structure of Formula (X). In an embodiment, each Z is Cl and $R^1$ and $R^2$ are each H; i.e., the compound of Formula (X) is 1,3-dichloro-4,6-dinitrobenzene and the Formula (XIII) dihalobenzene is 1,3-dichlorobenzene, which is commercially available.

The monoamination of the dihalodinitrobenzene can be carried out as described in U.S. Provisional Application No. 61/288,436, filed 21 Dec. 2009, which is by this reference incorporated in its entirety as a part hereof for all purposes. In step (a1), a suspension of the composition of Formula (X) in solvent is heated to a temperature in the range of about 60° C. to about 140° C., preferably about 100° C. to about 135° C., and more preferably about 130° C., to dissolve the composition of Formula (X) in a solvent. A suitable solvent is an organic solvent inert to the reaction such as an aliphatic dihydric alcohol, such as ethylene glycol ("glycol"). The resulting solution is contacted at that temperature with an aqueous solution of $HNR^7R^8$ for approximately two to four hours close to ambient pressure; the $HNR^7R^8$ solution is fed as it is consumed, as indicated by any convenient analytical technique (e.g., pH monitoring or measuring the flow rate of $HNR^7R^8$ in the gas phase above the reaction mixture).

In a preferred embodiment, the compound represented by Formula (XI) is 1-amino-3-chloro-4,6-dinitrobenzene. At least 2.00, preferably about 2.03 to about 2.07, equivalents of $HNR^7R^8$ are required. At reaction completion, the composition of Formula (XI) thereby produced can be directly isolated from the reaction mixture since it is only sparingly soluble in suitable solvents such as glycol at temperatures below 50° C.; impurities remain in solution, and net yields of 85% have been found at greater than 98% purity for 1-amino-3-chloro-4,6-dinitrobenzene specifically.

The composition of Formula (XI) is filtered, typically at about 60° C., and washed with solvent. In step (b1), the wet cake is then slurried with benzyl alcohol. About one to about two equivalents of base (e.g., NaOH as a slurry in benzyl alcohol, or a solution of the sodium salt of benzyl alcohol, Na—O—$CH_2$-Ph, also known as sodium benzyloxide) are added. The composition of Formula (XII) thereby produced is mixed with cold (e.g., about 10° C. to about 30° C. methanol/water (e.g., a 50:50 mixture of methanol and water by volume), and isolated by filtration, slurried with water, and transferred to a hydrogenation reactor as a suspension.

The composition of Formula (XII) is hydrogenated in step (c). The hydrogenation reactor contains a hydrogenation catalyst. Examples of suitable hydrogenation catalysts include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these, Pd/C and Pt/C, e.g., 10% Pd/C and 10% Pt/C, are preferred. The catalyst is typically used in the amount of about 0.5 to about 5.0 wt % metal based on 1-benzyloxy-3-amino-4,6-dinitrobenzene.

The hydrogenation reactor is purged with nitrogen and then hydrogen. Deaerated water is then added to the reactor. The aqueous suspension is contacted with hydrogen to form a reaction mixture. The reaction is carried out at a temperature in the range of about to 20° C. to 100° C., preferably about 60° C. to about 85° C., and a hydrogen pressure of about 45 to about 500 psi (0.31 to 3.45 MPa) preferably about 300 psi (2.07 MPa). Reaction continues for a time sufficient to consume about 6.5 to about 7.5 mol equivalents of hydrogen, thereby producing the composition of Formula (IX) and toluene. The toluene can be extracted using hexanes. The time required for the hydrogenation depends on the details of the specific set up but is typically about 2 hours.

The composition of Formula (XII) and the process for making it by steps (a1) and (b1) are a specific example of novel compositions represented by Formula (III)

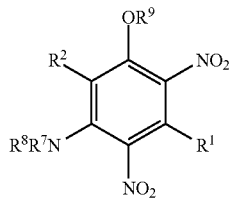

and a process for making them, wherein $R^9$ is n-propyl, isopropyl, a $C_4$ to $C_{18}$ tertiary alkyl, or a $C_7$ to $C_{18}$ substituted or unsubstituted benzyl. In general, the composition represented by Formula (III) wherein $R^9$ is benzyl, can be made by:

(a2) monoaminating a composition of Formula (X),

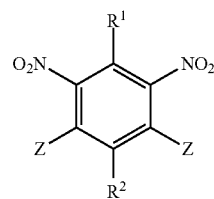

wherein each Z is independently Cl or Br, by heating a suspension of the composition of Formula (X) in solvent to a temperature in the range of about 60° C. to about 140° C. and contacting it with an aqueous solution of $HNR^7R^8$ to produce a composition of Formula (XI); and

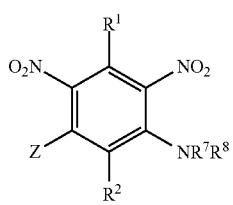

(b2) reacting the composition of Formula (XI) with the alcohol $R^9OH$ and about 1 to about 2 equivalents of NaOH or of the sodium salt of $R^9OH$, thereby producing a composition represented by Formula (III)

In the composition represented by Formula (XII), $R^9$ is benzyl. Another embodiment is represented by Formula (XIV), in which $R^1$, $R^2$, $R^7$, and $R^8$ are each H and $R^9$ is benzyl.

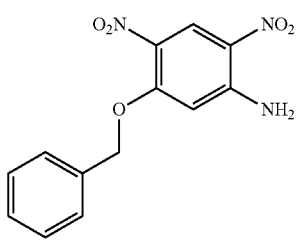

Novel compounds or compositions represented by Formula (II)

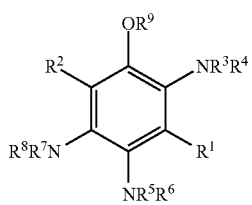

are O-alkylated versions of the compositions represented by Formula (I). In one embodiment, represented by Formula (XV), $R^1$, $R^2$, $R^3$, $R^4$, $R^5$, $R^6$, $R^7$, and $R^8$ are each H.

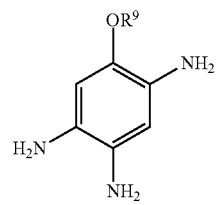

In another embodiment of the composition represented by Formula (II), $R^1$ and $R^2$ are each independently H, alkyl, or aryl, $R^3$ is H, $R^4$ is alkyl or H, and, of the four groups $R^5$, $R^6$, $R^7$, and $R^8$, any three are H and the fourth is H, alkyl, or aryl. An example of this embodiment is represented by Formula (XVI), in which $R^1$ is methyl, $R^2$, $R^3$, $R^4$, $R^5$, $R^6$, and $R^7$ are each H, and $R^8$ is methyl.

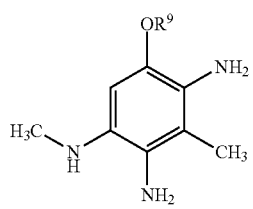

To produce compositions represented by Formula (I) or Formula (II) wherein at least one of $R^3$, $R^4$, $R^5$, and $R^6$ is alkyl or aryl, a compound of Formula (IX) or Formula (XVII),

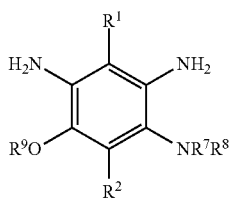

XVII respectively, could be prepared and then alkylated or arylated, am using an alky or aryl halide or pseudo halide as known by those skilled in the art. Alternatively, compounds of Formula (I) wherein at least one of $R^3$, $R^4$, $R^5$, and $R^6$ is alkyl or aryl could be produced by reductive amination of the compound of Formula (XII) using an aldehyde and hydrogen with the appropriate amine.

In another embodiment, a process is provided for the efficient production of novel, high-purity salts represented by Formula (IV) ("Formula (IV) salt")

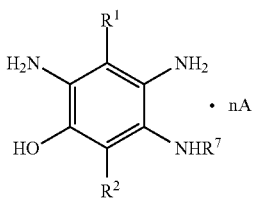

IV wherein n is 1 to 10 and A is an acid, e.g., HCl, acetic acid, $H_2SO_4$, or $H_3PO_4$, that can be converted to the free base (i.e., the composition of Formula (IX) wherein $R^8$ is H) or to a novel aromatic diacid complex of the free base with a diacid source, represented by Formula (V),

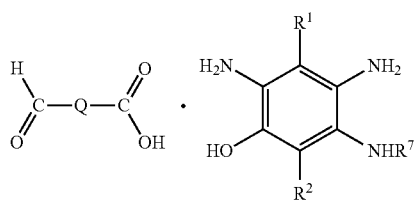

V of high enough purity for use in making a high molecular weight polymer material for producing high-performance fibers. The salt may also be a hydrate; one such example is 2,4,5-triaminophenol.3HCl.$xH_2O$ ("TAPH.3HCl.$xH_2O$"). In one embodiment, A is HCl and n is 2 to 4. In one embodiment, to prepare the Formula (IV) salt, the composition of Formula (IX) is prepared as described above, slurried in water, and contacted with an acid to form and precipitate the Formula (IV) salt. The mixture containing the precipitated Formula (IV) salt is then cooled to about 5° C. to about 15° C., stirred, and filtered. The Formula (IV) salt is then washed. It may be washed with deaerated aqueous acid, such as HCl (33%) and then optionally with deaerated ethanol or methanol to produce a wet cake material.

Whether aqueous acid or cold water is used as a wash, it may be possible to eliminate the ethanol or methanol wash and dry directly from aqueous wet cake or simply use the wet cake in subsequent processing. It is likely that in a commercial process one would only wash with $HCl_{aq}$ and, if desired, dry directly.

The resulting wet cake material (Formula (IV) salt) can be used in subsequent processing without drying or can be dried, for example at a pressure less than 400 Torr and a temperature of about 30° C. to about 50° C., under a stream of $N_2$. The dried product is preferably kept under nitrogen.

In another embodiment, a process is provided for preparing novel complexes of Formula (V),

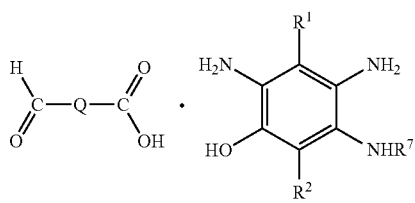

V wherein Q is a $C_6$ to $C_{20}$ substituted or unsubstituted monocyclic or polycyclic aromatic nucleus.

Examples of Q include without limitation:

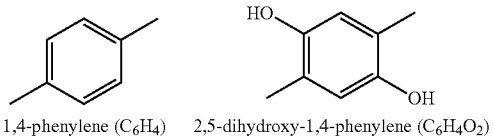

1,4-phenylene ($C_6H_4$)   2,5-dihydroxy-1,4-phenylene ($C_6H_4O_2$)

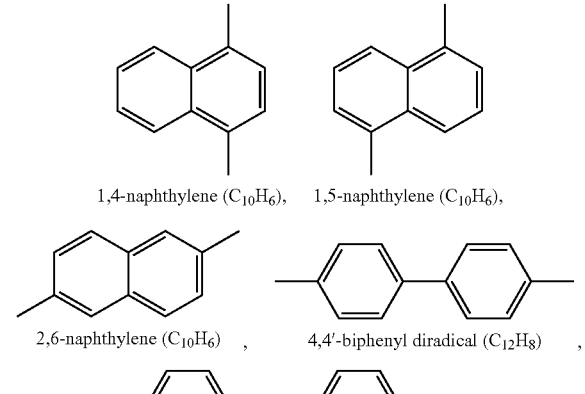

1,4-naphthylene ($C_{10}H_6$),   1,5-naphthylene ($C_{10}H_6$), 2,6-naphthylene ($C_{10}H_6$) ,   4,4'-biphenyl diradical ($C_{12}H_8$) , , and 4,4'-biphenyl ether diradical ($OC_{12}H_8O$)

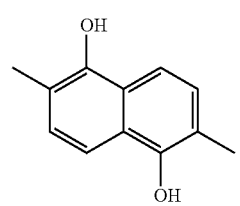

1,5 dihydroxy-2,6-napththylene ($C_{10}H_6O_2$).

One or more heteroatoms (such as N, O, S) may be present in the ring(s) of Q, for example, as shown below:

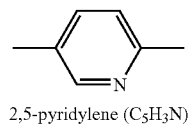

2,5-pyridylene ($C_5H_3N$)

In one embodiment, Q is represented by the structure of Formula (XVIII)

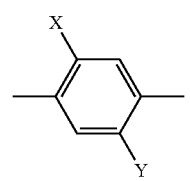

XVIII wherein X and Y are each independently selected from the group consisting of H, OH, SH, $SO_3H$, methyl, ethyl, F, Cl, and Br. Preferably, X=Y=OH (i.e., the diacid is 2,5-dihydroxyterephthalic acid) or X=Y=H (i.e., the diacid is terephthalic acid). When X=Y=H, the diacid is referred to as "XYTA".

In one embodiment ("Option A"), the Formula (IV) salt is precipitated and washed as described above, then slurried with water. Base (e.g., $NaHCO_3$), sufficient to neutralize the reaction mixture, and a diacid source are then added to the slurry to form and precipitate the complex, Formula (V). As used herein the term "diacid source" refers to the diacid HOOC-Q-COOH itself, the salt a disodium salt of HOOC-Q-COOH, a dipotassium salt to HOOC-Q-COOH, or mixtures thereof.

Alternatively ("Option B"), after the reaction mixture produced in hydrogenation step (c1) has been filtered and the toluene removed by extraction, typically using hexanes, the reaction mixture containing the composition of Formula (IX) (with $R^8$=H) can be combined directly with the base and the diacid source to form and precipitate the complex of Formula (V). In another alternative ("Option C"), filtered free base (Formula (IX) with $R^8$=H can be dissolved in about 1-2 equivalents of acid (e.g., HCl) and the solution so produced contacted with the base and the diacid source to form the complex of Formula (V).

In the complex described by Formula (V), it is important that the ratio of the free base (Formula (IX) with $R^5$=H) to the diacid source be 1:1. This allows the production of high molecular weight polymer from the complex and high strength fiber from the polymer. In some instances, including but not limited to, complexes wherein the free base is 2,4,5-triaminophenol ("TAPH"), i.e., the desired complex is represented by Formula (XIX),

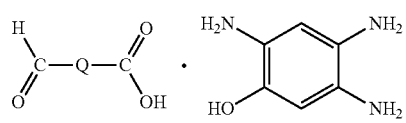

XIX the use of a strong base such as aqueous sodium hydroxide or aqueous potassium hydroxide in the Option A, B, or C process can cause the free base to diacid ratio in the complexes so produced to deviate from 1:1. In such cases, a preferred process is to dissolve the Formula (IV) salt, e.g., TAPH.2HCl, in water and contact that solution with the diacid source in an aqueous solution of a weak base such as $NaHCO_3$. As used herein, the term "weak base" denotes a base whose pKa at 25° C. is between about 6 and about 11. Such a base has a pKa sufficient to react with the HCl, but not to deprotonate the phenolic proton. This process can be performed under mild conditions, e.g., from ambient temperatures to about 50° C. The ratio of equivalents of the Formula (V) salt to equivalents of diacid source is from 1.0:1.0 to 1.5:1.0, preferably 1.025:1.00 to 1.10 to 1.00 equivalents.

Various designs are possible for combining the Formula (IV) salt with the diacid source and aqueous base to produce the complex. For example, the base and the diacid source are most conveniently added as a single solution. In other embodiments, the Formula (V) salt in an acid solution could be introduced into a vessel containing a basic diacid source solution, or the diacid source stream could be fed into the vessel containing the Formula (V) salt in an acid solution. Which design is best for a specific situation will be evident to one of skill in the art.

The Formula (V) complex is recovered from the reaction mixture by filtration at a temperature in of the range of about 5° C. to about 50° C., preferably about 10° C. to about 15° C., and washed with water and methanol, typically at a temperature in the range of about 15° C. to about 40° C., and then dried. The washed and dried Formula (V)·complex is kept under nitrogen to protect it from oxygen. It is of high enough quality and purity to produce polybenzimidazole polymer of high enough molecular weight to make high performance fibers.

The Option A embodiment discussed above can produce higher purity Formula (V) complex than Options B or C. On the other hand, Options B and C have fewer steps, generate less waste and also require less acid (e.g., HCl) and base (e.g., $NaHCO_3$), thus lessening raw material and handling costs. All disclosed embodiments produce polymer grade material suitable for the manufacture of high-performance fibers.

Oxygen is excluded throughout all steps of the processes of making the free base, the Formula (IV) salt, and the Formula (V) complex. Deaerated water and deaerated acid are used. A small amount of a reducing agent (e.g., about 0.5% tin powder) is optionally added to one or more of aqueous suspensions or aqueous solutions containing the triaminophenol free base, the Formula (IV) salt, or the Formula (V) complex during the process to reduce impurities caused by oxidation and to prevent further impurity formation by that route.

In another embodiment, novel polymer compositions are provided comprising a composition of Formula (I) or Formula (III) as a monomer. Articles comprising these polymers are also provided. Examples of such articles include without limitation fiber, film, and tape. In one embodiment, novel polymer compositions are provided comprising repeat units represented by Formula (VI).

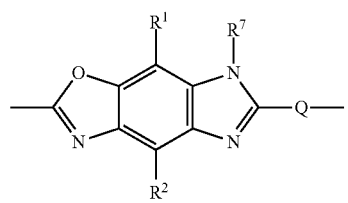

VI wherein $R^1$, $R^2$, and $R^7$ are each independently H, alkyl, or aryl; and Q is a $C_6$ to $C_{20}$ substituted or unsubstituted monocyclic or polycyclic aromatic nucleus as defined above.

Polymers comprising repeat units represented by Formula (VI) can be prepared at high molecular weight from a mixture of a triaminophenol salt represented by Formula (IV) (e.g., TAPH.2HCl) with HOOC-Q-COOH in polyphosphoric acid, or from a complex represented by Formula (V) at temperatures from about 100° C. to about 180° C.

In one embodiment, represented by Formula (XX), $R^1$, $R^2$, and $R^7$ are each H and Q is 1,4-phenylene.

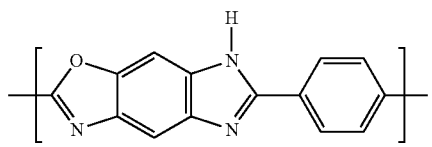

XX

The polymer represented by Formula (XX) can be made by polymerizing the 1:1 monomer complex of 2,4,5-triaminophenol with terephthalic acid ("TAPH.T complex"); or by polymerizing a mixture of a TAPH salt e.g., TAPH.2HCl) and terephthalic acid.

In another embodiment, represented by Formula (XXI), $R^1$, $R^2$, and $R^7$ are each H and Q is 2,5-dihydroxy-1,4-phenylene ($C_6H_4$).

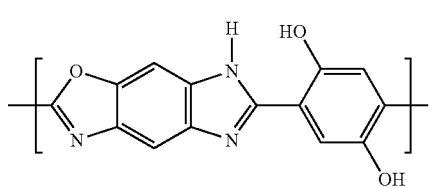

XXI

The polymer represented by Formula (XX) can be made by polymerizing the 1:1 monomer complex of 2,4,5-triaminophenol with 2,5-dihydroxyterephthalic acid ("TAPH.DHTA complex"); or by polymerizing a mixture of a TAPH salt (e.g., TAPH.2HCl) and 2,5-dihydroxyterephthalic acid.

The polymerization of the monomer complex is typically carried out in a reactor suitably equipped with connections for purging with inert gas, applying a vacuum, heating and stirring. Monomer complex, P-2O$_5$, polyphosphoric acid ("PPA") and powdered metal (for example, tin or iron metal) are typically added to the reactor. The reactor is typically purged, heated and mixed to effect polymerization.

In a preferred embodiment, about 20 parts by weight of monomer complex, about 10 parts of $P_2O_5$, 100 parts of PPA, and about 0.1 parts tin or iron metal are added to a suitable reactor. The contents of the reactor are stirred at about 60 rpm and heated to about 100° C. for about one hour under vacuum with a slight nitrogen purge. The temperature is typically raised to at least 110° C., preferably at least about 120° C., and preferably not more than 140° C. for a few more hours, preferably about four hours. The temperature is then raised and held at a higher temperature, at least about 130° C., more typically at least about 140° C., and preferably at about 150° C. for about an hour, more preferably about three hours. The temperature is subsequently then raised and held at a higher temperature, at least about 150° C., more typically at least about 170° C., and preferably at about 180° C. for about an hour, more preferably about three hours. The reactor is typically flushed with nitrogen and a sample of the polymer solution is taken for viscosity determination.

Typically, the polymers so produced from monomer complexes form polybenzarenazoles that are characterized as providing a polymer solution having an inherent viscosity of at least about 29 dl/g at 30° C. at a polymer concentration of 0.05 g/dl in methanesulfonic acid. In certain embodiments, the metal powder is present in an amount of about 0.1 to about 0.5 weight percent based on monomer complex.

In certain embodiments, the reaction mixture includes polyphosphoric acid having an equivalent $P_2O_5$ content of at least about 81 percent after polymerization, and more preferably at least about 86 percent after polymerization. In certain embodiments, the reaction mixture includes polyphosphoric acid having an equivalent $P_2O_5$ content of at least about 81 percent after contacting, in polyphosphoric acid, the monomer complex with metal powder, the metal powder added in an amount of from about 0.05 to about 0.9 weight percent, based on the total monomer weight and polymerizing the monomers in polyphosphoric acid to form the polymer solution. In certain of these embodiments, the ratio of equivalents of the triaminophenol to the diacid source is typically at least about 1 to 1, more typically at least about 1.05 to 1, even more typically at least about 1.075 to 1, and further typically at least about 1.15 to 1.

A solution of such polymers at about 10 to about 30 wt % in polyphosphoric acid can be used to prepare high strength fiber, films, and tapes, which can be used, for example, as reinforcement materials for thermoplastic and thermoset matrices. Fibers may also be cut and used as staple fiber or, when fibrillated, as pulp. Useful articles comprising the polybenzarenazole polymers described herein include without limitation: protective apparel (e.g., body armor, industrial gloves, flame retardant apparel); aircraft applications (e.g., components of aircraft cabin, flooring and interiors, landing gear doors; rotor blades; space craft; maritime vessels; automotive components (e.g., tires, friction and sealing applications, brake pads, belts, gaskets, hoses, composites, vehicular armor); sports equipment; and personal electronics.

EXAMPLES

This invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

All water used was deaerated and de-ionized water. The examples were carried out under exclusion of oxygen.

The meaning of abbreviations is as follows: "ACDNB" means 1-chloro-3-amino-4,6-dinitrobenzene, "BOB" means 1-benzyloxy-3-amino-4,6-dinitrobenzene, "cm" means centimeter(s), "d" means density, "DADNB" means 1,3-diamino-4,6-dinitrobenzene, "DCDNB" means 1,3-dichloro-4,6-dinitrobenzene, "dl" means deciliter(s), "equiv" means equivalent(s), "g" means gram(s), "gal" means gallon, "GC" means gas chromatography, "$^1$H-NMR" means proton nuclear magnetic resonance spectroscopy, "h" means hour(s), "L" means liter(s), "mL" means milliliter(s), "min" means minutes, "mol" means mole(s), "MPa" means megapascals, "PPA" means polyphosphoric acid, "psi" means pounds per square inch, "rpm" means revolutions per minute, and "$\eta_{inh}$" means inherent viscosity.

Example 1

Preparation of DCDNB

To a 1 L 3-neck round bottom flask equipped with external ice cooling, mechanical stirrer, addition funnel, $N_2$ inlet, and thermometer was added 126 g (2 mol) fuming nitric acid (d=1.54 g/cm$^3$), followed by 208 g sulfuric acid and 508 g 30% oleum (2.2 molar equiv $SO_3$), maintaining a temperature between 10 and 40° C. Subsequently, 140 g (0.95 mol) 1,3-dichlorobenzene (Toray Ltd., Tokyo, Japan, >99% purity) were added over a time period of 90 min while maintaining a temperature of about 5° C. The ice bath was removed, and the reaction mixture was allowed to warm up to room temperature. It was then heated from room temperature to 100° C. over a time period of 45 min. At that point, a small sample of crude product was taken from the reaction vessel and poured into ice water. The crude product was extracted with methylene chloride. Analysis by GC and $^1$H-NMR indicated a reaction selectivity for 1,3-dichloro-4,6-dinitrobenzene of 92%. After 15 min at 100° C., the reaction mixture was allowed to cool to room temperature over 2 h and then cooled to 5° C. over 30 min, after which it was filtered through a glass fritted funnel and washed with 300 mL water followed by 200 mL 10% aqueous $NH_3$ solution. Analysis indicated a net content of about 184 g of >98% pure product (~80% net yield) and the dry mass content of the wet cake was about 90%.

Example 2

Preparation of ACDNB from DCDNB

A three-necked flask was equipped with a thermocouple, magnetic stirrer, septa through which a tube was added for the addition of the ammonium hydroxide solution and reflux condenser with gas outlet. The DCDNB and ethylene glycol were added to the flask. The ammonium hydroxide was pumped into the vessel at a rate of 0.607 mL/min at a temperature of 138° C. A total of 6.7 moles of ammonium hydroxide were added. Conversion to product was controlled by GC analysis. The reaction suspension was allowed to cool to 60° C. before it was filtered and the yellow-to-bronze colored fine crystalline product was washed with two portions of about 50 mL of 60° C. ethylene glycol followed by 2×50 mL water. GC analysis showed that the reaction solution contained less than 1% 1,3-dichloro-2,4-dinitrobenzene and no more than 3% 1,3-diamino-2,4-dinitrobenzene. The net yield was about 75% and the purity was >97%.

Example 3

Preparation of 1-benzyloxy-3-amino-4,6-dinitrobenzene ("BOB") from ACDNB

A three-necked 2 L flask was equipped with a thermocouple, magnetic stirrer and reflux condenser with gas outlet. The gas outlet was equipped with a three-way-splitter connecting the outlet to an oil bubbler and an $N_2$ line. The ACDNB and benzyl alcohol were added to the flask and heated to 50° C. while under a $N_2$ blanket. The solid sodium hydroxide was added to the reaction as a ground powder in 10 equal portions over 3 h such that the reaction temperature did not exceed 55° C. During the course of the reaction, a deep-red color was produced along with a slight exotherm of a few degrees. Conversion to product was controlled by LC analysis. After addition of 1.05 equivalent of base the reaction was allowed to return to room temperature. The reaction suspension was poured into a 50:50 wt % solution of cold methanol and water. This mixture was stirred and then filtered. The solid product of light bronze color was further rinsed with another portion of 50:50 methanol and water. After a final rinse with cold methanol, the filter cake was air-dried. The net yield was about 80% and the purity was 96%.

Example 4

Preparation of TAPH.2HCl from BOB

A 1-gal (3.79 L) stirred Hastelloy autoclave was charged with 125 g of BOB prepared in Example 3 and 3.6 g of 10% PVC (dry basis, 50% water). The autoclave was purged 10 times with $N_2$ and 5 times with $H_2$ at 90 psi (0.62 MPa). Subsequently, 300 mL of deaerated water (purged with $N_2$ overnight) were added and the mixture was pressurized at 60° C. to 300 psi (2.07 MPa). Hydrogenation was continued for a total time of about 80 min with an approximate uptake of 2.7 moles of $H_2$ (6.5 equiv). The excess hydrogen was released and the autoclave was cooled to 40° C. and purged twice with $N_2$, after which 80 g of deaerated $HCl_{aq}$ (36.3%, by titration) and 175 g of water were added. The mixture was stirred for 1 hour, then passed through a metal CUNO filter to remove catalyst. The autoclave was rinsed with 30 mL of deaerated water. The solution was directly charged into a purged 2 L vessel.

The reaction mixture was extracted with 2×200 mL portions of hexanes, and the organic phase was discarded. The aqueous phase was filtered through a filter packed with celite followed by carbon black and sand. About 0.1 g of Sn powder was added to the filtrate. The mixture was neutralized to pH 6 with aqueous sodium hydroxide (50% wt) and the free base, TAPH, was isolated by filtration. The free base was subsequently combined with water to form a 50% wt slurry. In a separate flask, 300 g (10 equivalents) of concentrated aqueous HCl (approximately 36% wt) was cooled to about 5° C. The free base TAPH slurry was added slowly to the stirred cold HCl solution while maintaining a solution temperature of about 5° C. After stirring for an additional 2 h at 5° C., the TAPH hydrochloride salt was isolated by filtration and washed twice with about 50 mL methanol. The net yield of TAPH hydrochloride salt isolated was about 60% and the purity was >99%. Elemental analysis: C, 33.56%, N, 19.23%, H, 5.07%, Cl, 33.28%. An X-ray structural determination confirmed that the product was TAPH.2HCl.

Example 5

Preparation of TAPH.2HCl from BOB

A L stirred Hastelloy autoclave was charged with 120 g (0.415 moles) of 1-benzyloxy-3-amino-4,6-dinitrobenzene ("BOB"), and 3.6 g of 1.0% Pd/C. The autoclave was purged 10 times with $N_2$ and 5 times with $H_2$ at 90 psi (0.62 MPa). Subsequently, 290 g of deaerated water (purged with $N_2$ overnight) was added and the mixture was pressurized at 60° C. to 300 psi (2.07 MPa). Hydrogenation was continued for a total time of about 2.5 h. The excess hydrogen was released and the autoclave was cooled to 40° C. and purged twice with $N_2$, after which 80 g of $HCl_{aq}$ in 145 g deaerated water was added. The mixture was stirred for one hour, and then passed through a carbon bed filter at about 40° C. to remove catalyst. The filter was rinsed with 30 mL of water. The TAPH.2HCl solution was directly charged into holdup vessel under $N_2$ containing 5 g of Sn powder.

Example 6

Preparation of TAPH.DHTA from TAPH.2HCl Solution 6.06 g of $K_2$DHTA (22.08 mmol) along with 2.69 g of sodium bicarbonate (32.02 mmol) was added to a reaction vessel. This was followed by the addition of 75 g of deaerated water and heating to 75° C. About 3175 g of 0.18M TAPH.2HCl salt solution (24.3 mmol) made as described in Example 5 was added to another reaction vessel. The hot solution of $K_2$DHTA was subsequently added dropwise into the TAPH.2HCl salt solution at room temp., with fast stirring, over a period of 10 minutes, which resulted in precipitation of a light brown solid. This mixture was then cooled to room temp., with stirring, for 1.5 hours. The mixture was subsequently filtered and washed with ethanol (50 mL). The solid beige product was allowed to dry for 18 hours under vacuum. $^1$H-NMR analysis revealed the TAPH-DHTA ratio as being (1.00:1.01).

Example 7

Preparation of TAPH.T from TAPH.2HCl Solution 3.03 g of terephthalic acid (19.872 mmol) along with 2.05 g of sodium bicarbonate (40.738 mmol) was added to a reaction vessel. This was followed by the addition of 54 g deaerated water and heating to 75° C. About 30.375 g of 0.18 M TAPH.2HCl salt solution (21.87 mmol) made as described in Example 5 was added to another reaction vessel along with 2.25 g of sodium bicarbonate (26.83 mmol). The hot solution of terephthalic acid was subsequently added dropwise into the TAPH.2HCl salt solution at room temp., with fast stirring, over a period of 10 minutes, which resulted in precipitation of a purple solid. This mixture was then cooled to room temp., with stirring, for 1.5 hours. The mixture was subsequently filtered and washed with ethanol (50 mL). The solid pink product was allowed to dry for 18 hours under vacuum. $^1$H-NMR analysis revealed the TAPH-T ratio as being (1.00: 1.01).

Example 8

Polymerization of TAPH.T Complex in Polyphosphoric Acid

Into a clean dry 200 mL glass tubular reactor having an inside diameter of 4.8 cm, equipped with the necessary connections for purging nitrogen and applying a vacuum, and around which a heating jacket was arranged and which further contained double helix shaped basket stirrer, was charged 14.7 g of monomer complex, 10.92 g $P_2O_5$, 54.42 g of PPA with a % $P_2O_5$ equivalent to 85.5%, and 0.07 g Fe powder. The stirrer was turned on at 100 rpm and the contents were heated to 100° C. for one hour under vacuum. The temperature was raised and held at 120° C. for 18 hours. The temperature was raised and held at 150° C. for 4 hours. The temperature was raised and held at 180° C. for 4 hours. The reactor was flushed with nitrogen gas ("$N_2$") and a sample of the polymer solution was diluted with methane sulfonic acid to 0.05% concentration. The $\eta_{inh}$=6.6 dl/g.

Example 9

Polymerization of TAPH.DHTA Complex in Polyphosphoric Acid (Glass Tubular Reactor)

Into a dean dry 200 mL glass tubular reactor having an inside diameter of 4.8 cm, equipped with the necessary connections for purging nitrogen and applying a vacuum, and around which a heating jacket was arranged and which further contained double helix shaped basket stirrer, was charged 10.17 g of TAPH complex, 5.81 g of $P_2O_5$, 64.1 g of PPA with a % $P_2O_5$ equivalent to 85.4%, and 0.05 g Fe powder. The stirrer was turned on at 100 rpm and the contents were heated to 100° C. for one hour under vacuum. The temperature was raised and held at 120° C. for 18 hours. The temperature was raised and held at 150° C. for 3 hours. The temperature was raised and held at 180° C. for 3 hours. The reactor was flushed with nitrogen gas ("$N_2$") and a sample of the polymer solution was diluted with methane sulfonic acid to 0.05% concentration. The $n_{inh}$ was 29.3 dl/g.

Example 10

Polymerization of TAPH.DHTA Complex in Polyphosphoric Acid (Twin Cone Reactor)

The following were combined in a clean dry 2CV Model DIT Mixer (available from Design integrated Technology, Inc, Warrenton, Va.).
  a) 71.62 grams of Polyphosphoric Acid (PPA) with a concentration of 85.4% $P_2O_5$,
  b) 10.57 grams of $P_2O_5$,
  c) 0.07 grams of Fe powder (325 mesh and available from VWR scientific; this amount is 0.4% based on weight of TAPH.DHTA complex), and
  d) 17.8 grams of TAPH DHTA complex (one to one complex of 2,4,5-triaminophenol (TAPH) and 2,5-dihydroxyterephthalic acid (DHTA)).

The CV Model was a jacketed twin cone reactor that was heated by the circulation of hot oil through the jacket. This reactor used intersecting dual helical-conical blades that intermesh throughout the conical envelope of the bowl. The mixer blades were started and set at about 80 rpm. The reactor was swept with dry $N_2$ gas followed by a vacuum. The temperature of the reaction mixture was measured throughout using a thermocouple. The temperature of the reaction mixture was raised to 100° C. and under vacuum held for 1 hour. The temperature of the reaction mixture was raised to 120° C. and held for 18 hours. Next, the temperature of the reaction mixture was raised to 150° C. and held for 3 hours. Next, the temperature of the reaction mixture was raised to 180° C., and held for 3 hours. The mixer was purged with nitrogen and the polymer solution was discharged into a glass vessel. The polymer was removed from the mixer in the form of a solution in PPA. A sample of the polymer was separated from the solution and then diluted with methane sulfonic acid ("MSA") to a concentration of 0.05% polymer solids. The inherent viscosity of the polymer sample was 29.92 dl/g.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight. When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true or present and both A and B are true (or present.

When the term "about" is used in describing a value or an end-point of a range, the disclosure should be understood to include the specific value or end-point referred to. Use of "a" or "an" are employed to describe elements and components of the invention. This is done merely for convenience and to give a general sense of the invention. This description should be read to include one or at least one and the singular also includes the plural unless it is obvious that it is meant otherwise.

The materials, methods, and examples herein are illustrative only and, except as specifically stated, are not intended to be limiting.

What is claimed is:

1. A process comprising the steps
   (d1) monoaminating a composition described by Formula (X),

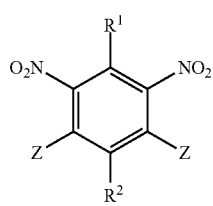

wherein each Z is independently Cl or Br and $R^1$ and $R^2$ are each independently H, alkyl, or aryl; by heating a suspension of the composition of Formula (X) in solvent to a temperature in the range of about 60° C. to about 140° C. and contacting it with an aqueous solution of at least 2.0 equivalents $HNR^7R^8$ to produce a composition of Formula (XI), wherein $R^7$ and $R^8$ are each independently H, alkyl or aryl, or may be joined to form an aliphatic ring structure;

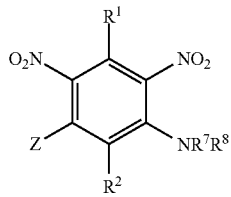

(e1) reacting the composition of Formula (XI) with benzyl alcohol and at least 1.0 equivalent of NaOH or of sodium benzyloxide to produce a composition of Formula (XII);

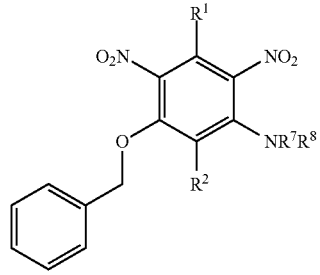

(f1) hydrogenating the composition of Formula (XII) by contacting the reaction mixture formed in step (b1) with hydrogen at a pressure in the range of about 0.31 to about 3.45 MPa and a temperature in the range of about 20° C. to about 100° C. for sufficient time to hydrogenate the composition of Formula (XII), thereby producing a reaction mixture comprising a composition of Formula (IX) and toluene

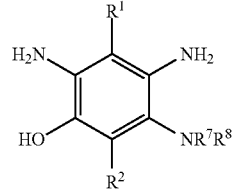

(d1) the reaction mixture formed in step (a) with an aqueous solution comprising 1 to 2 equivalents of acid per mol of 2,4,5-triaminophenol and, optionally, heating the solution, thereby dissolving the 4,4,5-triaminophenol;
(e1) filtering the reaction mixture, thereby removing the spent hydrogenation catalyst;
(f1) extracting the toluene from the reaction mixture; and
(g1) adjusting the pH of the extracted, filtered reaction mixture to a value between about 5 and about 7, by adding a base wherein said base does not increase the solubility of the Formula (IX) composition, thereby precipitating the composition of Formula (IX) from the reaction mixture.

2. The process of claim 1 wherein each Z is Cl.

3. The process of claim 1 wherein $R^1=R^2=H$.

4. The process of claim 1 wherein $R^7=R^8=H$.

5. The process of claim 1 wherein the in step (c1) is 10% Pd/C or 10% Pt/C.

6. The process of claim 1 further comprising slurrying the composition of Formula (IX) in water to form a mixture and contacting the mixture with an acid A, thereby forming and precipitating the Formula (IV) salt

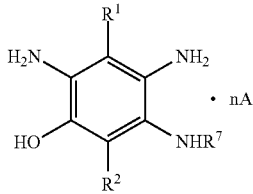

IV wherein n is 1 to 10 and A is selected from the group consisting of HCl, acetic acid, $H_2SO_4$, and $H_3PO_4$.

7. The process of claim 6 wherein n is 2 to 3 and A is HCl.

8. The process of claim 6 further comprising cooling the mixture containing the precipitated Formula (IV) salt to a temperature from about 5° C. to about 15° C., stirring the mixture, filtering the mixture to isolate the Formula (IV) salt, and washing the Formula (IV) salt.

9. The process of claim 6 further comprising slurrying or dissolving the Formula (IV) salt in water and then adding aqueous base and a diacid source to the slurry to form and precipitate the complex represented by Formula (V)

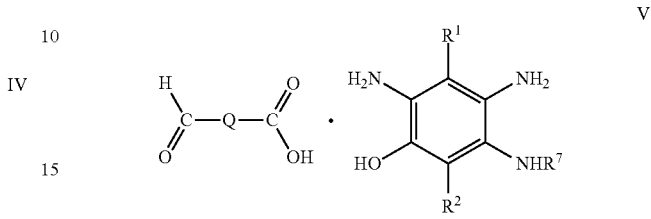

V wherein the diacid source is HOOC-Q-COOH, the salt a disodium salt of HOOC-Q-COOH, a dipotassium salt of HOOC-Q-COOH, or mixtures thereof, wherein Q is a $C_6$ to $C_{20}$ substituted or unsubstituted monocyclic or polycyclic aromatic nucleus.

10. The process of claim 1 wherein the toluene is extracted in step (f1) using hexanes.

* * * * *